US00PP36918P2

(12) United States Plant Patent
Hansen

(10) Patent No.: US PP36,918 P2
(45) Date of Patent: Sep. 2, 2025

(54) ***VERNONIA* PLANT NAMED 'Prairie Princess'**

(50) Latin Name: ***Vernonia* hybrid**
Varietal Denomination: Prairie Princess

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,117

(22) Filed: Jul. 25, 2024

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 5/02
See application file for complete search history.

*Primary Examiner* — Kent L Bell

(57) ABSTRACT

A new and distinct cultivar of *Vernonia* plant named 'Prairie Princess' with very rounded mound habit; dark olive-green with a purplish blush early in the season, linear foliage and numerous inflorescences, on heavily-branched stems, containing rosy-purple disk florets beginning in late summer and continuing for about six weeks. The new plant is useful for landscaping, as a specimen or en masse and as a cut flower.

1 Drawing Sheet

Botanical designation: *Vernonia* hybrid.
Cultivar denomination: 'Prairie Princess'.

STATEMENT REGARDING PRIOR DISCLOSURES UNDER 37 CFR 1.77 (b) (6)

The first offer for sale of the claimed plant was made by Walters Gardens, Inc. on Aug. 22, 2023, with a first sale on Sep. 24, 2023, to Centerton Nursery, Inc. Walters Gardens, Inc. obtained the plant and all information relating thereto, from the inventor. No plants of *Vernonia* 'Prairie Princess' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct cultivar of Ironweed plant herein referred to as *Vernonia* 'Prairie Princess', by the cultivar name 'Prairie Princess', or as the new plant. The new plant represents a new herbaceous perennial grown for landscape use. 'Prairie Princess' was selected by the inventor as a single seedling resulting from an insect pollination in the summer of 2018 of a proprietary, unreleased, unnamed seedling known only by the breeder code 17-14-10 (not patented) times a proprietary, unreleased, unnamed seedling known only by the breeder code 17-14-11 (not patented) in a research facility of a wholesale perennial grower based in Zeeland, MI, USA. The seeds from this cross were collected in the fall of 2018. The single unique seedling was then isolated and compared in subsequent years to other *Vernonia* and subsequently found to be different from all cultivars known to the discoverer and eventually given the breeder code 18-8-3.

Asexual propagation at the same nursery in Zeeland, MI, USA by shoot tip cuttings since spring of 2021 has shown 'Prairie Princess' to be stable and reproduce true to type in successive generations.

SUMMARY OF THE PLANT

*Vernonia* 'Prairie Princess' has not been observed in all possible environmental conditions. The phenotype may vary slightly with changes in environments such as light intensity, fertility, water availability, etc. without, however, any variation in genotype.

*Vernonia* 'Prairie Princess' is distinct from all cultivars known to the inventor in the following traits:

1. Compact, very rounded mound of about 85 cm tall and 110 cm wide;
2. Linear foliage of dark olive-green with a purplish blush early in the season, and resistant to powdery mildew;
3. Heavily-branched peduncles with densely-packed inflorescences covering the top half of the plant;
4. Inflorescences of rosy purple disk florets;
5. Long flowering period beginning late summer and continuing for about six weeks.

Plants of *Vernonia* 'Prairie Princess' are most similar to 'Southern Cross' (not patented), 'Summer's End' U.S. Plant Pat. No. 33,602, 'Summer's Surrender' U.S. Plant Pat. No. 28,475, and 'Summer's Swan Song' U.S. Plant Pat. No. 28,556.

'Southern Cross' is slightly larger in habit with broader foliage that does not develop a purplish tint in high light 'Summer's End' is both taller and broader than the new plant, and the foliage does not develop a purplish tint 'Summer's Surrender' is significantly taller and much wider in habit, and the foliage is both longer and broader without developing a purplish tint. 'Summer's Swan Song' is shorter in habit, the foliage is longer and broader and does not develop a purplish tint.

The parent plants 17-14-10 and 17-14-11 have a taller and more open habit and purplish blush on the foliage.

BRIEF DESCRIPTION OF THE DRAWINGS

The color drawings illustrate the overall characteristics of *Vernonia* 'Prairie Princess' as a five-year-old plant in a full-sun trial garden in Zeeland, Michigan. The colors are as true as reasonably possible given the technology available. The color values may vary slightly depending on light intensity and quality.

DETAILED BOTANICAL DESCRIPTION

Figure 1:
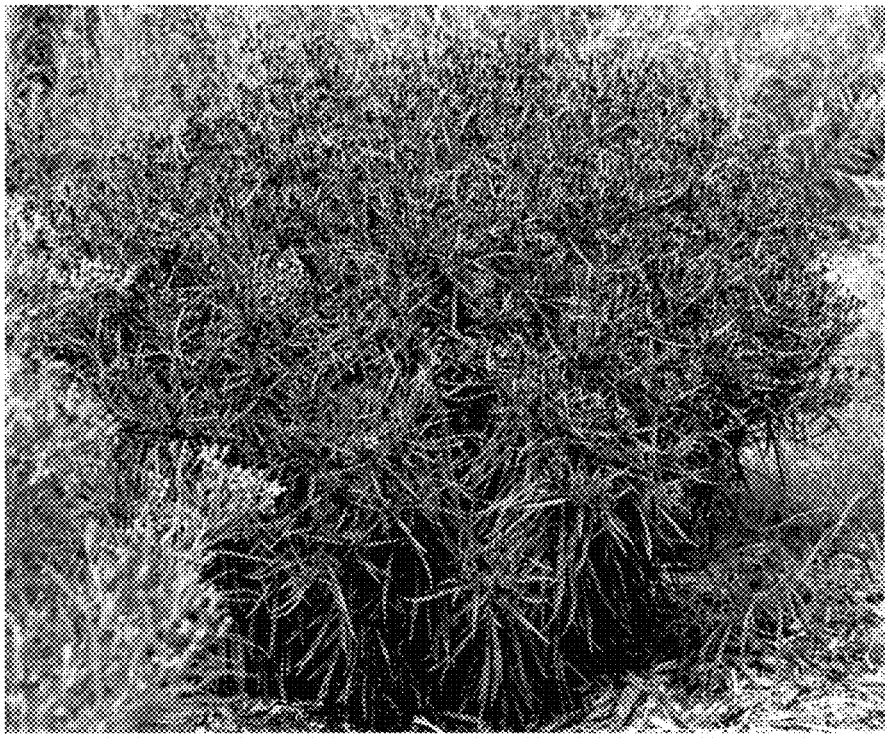
FIG. 1 shows the new plant in a full-sun trial garden.
Figure 2:
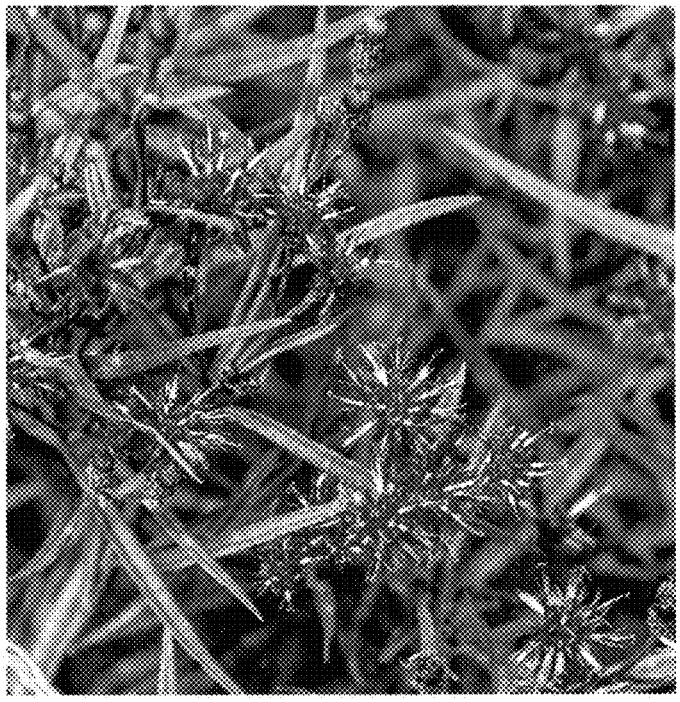
FIG. 2 shows a close-up of the inflorescences and buds of the new plant.

The following description of the new plant is based on a five-year-old plant growing in a full-sun trial field in Zeeland, MI, USA. Except for ordinary dictionary color usage, color references are according to The Royal Horticultural Society Colour Chart, 2015 edition.

Parentage: Female or seed parent 17-14-10; male or pollen parent 17-14-11;

Asexual propagation: Apical shoot tip cuttings, about 3 to 4 weeks to initiate roots; time to finish as #1 field grown size about 6 months;

Roots: Fibrous; heavily branched; color of older roots near RHS 199C depending on soil matrix, and young active roots near RHS NN155B;

Plant habit: Herbaceous, winter-hardy, rhizomatous, perennial mound with stiff upright stems; to about 85 cm tall and 110 cm wide;

Leaves: Alternate; simple; linear; acute apex; base attenuate; margin micro-serrulate; adaxial and abaxial glabrous and matte;

Leaf quantity: About 70 per stem below branched peduncle;

Leaf size: To about 13.8 cm long and about 0.8 cm wide;

Leaf color: Young expanding leaves adaxial between RHS 147B and RHS 147A and abaxial distally between RHS 147B and RHS 146A with the 5 mm base between RHS 59A and RHS N186C; mature adaxial nearest RHS NN137A and abaxial nearest RHS NN137C;

Foliar fragrance: None noted;

Veins: Pinnate; glabrous adaxial and abaxial;

Vein color: Adaxial RHS 148B on midrib and secondary; abaxial midrib nearest RHS 148B and secondary nearest RHS NN147C;

Petiole: Sessile;

Stems: Upright; cylindrical; micro-puberulent; stiff; heavily branched; surface matte; approximately 70 per plant;

Stem size: To about 51 cm tall below branches and about 8 mm diameter;

Stem color: Proximal portion between RHS 146B and RHS 146C with longitudinal lightly blushed stripes of RHS 183B, distal stem nearest RHS 147B with moderately blushed stripes to nearly solid RHS 183B; and nodes nearest RHS 183B;

Branches: Cylindrical; micro-puberulent; up to 12 per main stem in upper 10 cm of peduncle; to about 18 cm long and 0.2 cm diameter;

Branch color: Between RHS N186C and RHS N186B;

Peduncle: Cylindrical; micro-puberulent; strong; upright; to about 6 mm long and 1 mm diameter; color between RHS N186C and RHS 186B;

Pedicel: Of individual tepal and disk flowers too small to measure or observe color;

Inflorescence: Capitula organized as compound corymbiform; composite consisting of about 26 disk florets per capitulum and no ray florets; on heavily branched terminal stems; individual inflorescence about 18 mm diameter, about 18 mm tall from bottom of involucral bracts to top of exerted style; attitude upright in center and outwardly toward exterior; produced on heavily-branched stems;

Receptacle: About 5 mm tall and 4 mm across; color nearest RHS 148C;

Inflorescence fragrance: Not detected;

Phyllaries: About 60 per capitulum; linear to deltoid; narrowly acute apex; truncate base; margin entire; glabrous; to about 6 mm long and 2 mm across at base, decreasing in size distally; divergent, not adpressed.

Phyllary color: Adaxial nearest RHS N186C distally and RHS 146D proximally, abaxial nearest RHS N186C distally and proximally between RHS 146B and RHS 146A;

Flowering period: Beginning late summer for about six weeks; individually for about 3 to 5 days;

Inflorescence longevity: 6 to 8 days;

Flower buds: Oblong; with tepals still erect 8 mm tall and 1 mm across;

Inflorescence bud color: Disk florets while still upright exposed abaxial tepal color between RHS 79B and RHS N79B;

Disk florets: Imperfect; complete; typically about 26 per inflorescence; about 15 mm long and 3 mm diameter;

*Corolla tube.*—Consisting of five linear tepals; about 11 mm long and 3 mm across at apices.

*Tepals.*—Five; apex acute; margin entire; glabrous and slightly lustrous adaxial and abaxial; fused in the basal 8 mm; to about 11 mm long and about 0.5 mm wide at fusion.

*Tepal color.*—Distal half of adaxial and abaxial between RHS N81A and RHS N87A, proximal half of adaxial and abaxial between RHS N87D and RHS 84D.

*Pistil.*—Single; to about 17 mm long.

*Style.*—Single; cylindrical; about 14 mm long and about 0.2 mm diameter; distally enclosed in anther column; color proximal two-thirds nearest RHS NN155D, distal one-third between RHS N81A and RHS N87A.

*Stigma.*—Bifid, cylindrical; about 1 mm long and 0.1 mm diameter; color between RHS N81A and RHS N87A.

*Ovary.*—Elliptical; about 2 mm long and 0.7 mm diameter; color nearest RHS NN155B with faint blush nearest RHS N78B.

*Stamen.*—5; adnate around the style.

*Anther.*—Longitudinal; introrse; individually oblong; to about 4 mm long and about 1mm across; color nearest RHS 168D.

*Pollen.*—Moderate; color nearest RHS 168D.

*Pappus.*—About 25; straight; thin; 6 mm long and less than 0.1 mm diameter; color nearest RHS N79A.

Seed: Achene; conical; about 1 mm long and 0.5 mm wide, apex acute; color nearest RHS 161C;

*Vernonia* 'Prairie Princess' is resistant to powdery mildew (*Golovinomices* sp.) and maintains most of the lower foliage through the season. No susceptibility and resistance of other diseases and pest that are common to other Ironweed cultivars has been observed.

The new plant is winter hardy and grows well in USDA zones 4 through 9 and resists lodging from heavy rains.

I claim:

1. A new and distinct cultivar of *Vernonia* plant named 'Prairie Princess' as herein described and illustrated.

* * * * *